United States Patent [19]

Fink

[11] Patent Number: 5,431,053
[45] Date of Patent: Jul. 11, 1995

[54] ULTRASONIC IMAGING METHOD AND APPARATUS, USING TIME INVERSION OR SIGNALS

[75] Inventor: Mathias Fink, Meudon, France

[73] Assignee: Universite Paris VII, Paris, France

[21] Appl. No.: 971,166

[22] Filed: Nov. 4, 1992

[30] Foreign Application Priority Data

Nov. 5, 1991 [FR] France .................. 91 13629

[51] Int. Cl.⁶ .......................................... G01N 29/06
[52] U.S. Cl. ........................................ 73/602; 73/628; 73/598; 73/596
[58] Field of Search ............... 73/602, 606, 603, 598, 73/600, 596, 641; 364/507, 508; 367/95, 124, 125

[56] References Cited

U.S. PATENT DOCUMENTS 4,463,608 8/1984 Takeuchi et al. ................ 73/606
5,092,336 3/1992 Fink ........................ 128/660.03

FOREIGN PATENT DOCUMENTS 826774 1/1960 United Kingdom .
2074732 11/1981 United Kingdom .

*Primary Examiner*—Hezron E. Williams
*Assistant Examiner*—Nashmiya Ashraf
*Attorney, Agent, or Firm*—Larson & Taylor

[57] ABSTRACT

A method for internal inspection of pieces having an interface with a propagation medium, is described. The steps include: illuminating a reference piece with an ultrasound beam from a first array of transducers excited by stored excitation signals; sensing reflected echo signals received by transducers, which may be the transducers of the first array, and storing the waveforms and time distribution thereof; simultaneously sensing refracted signals, received by transducers belonging to a second array placed opposite to the the first relative to the piece and storing the waveforms and time distribution of the signals received by the transducers of the second array; replacing the reference piece with a piece to be inspected having the same shape and occupying the same location, and applying, to each of the transducers, energization signals obtained by time reversal of the stored waveforms and time distribution; and sensing the signals received by the transducers of the second network.

8 Claims, 3 Drawing Sheets

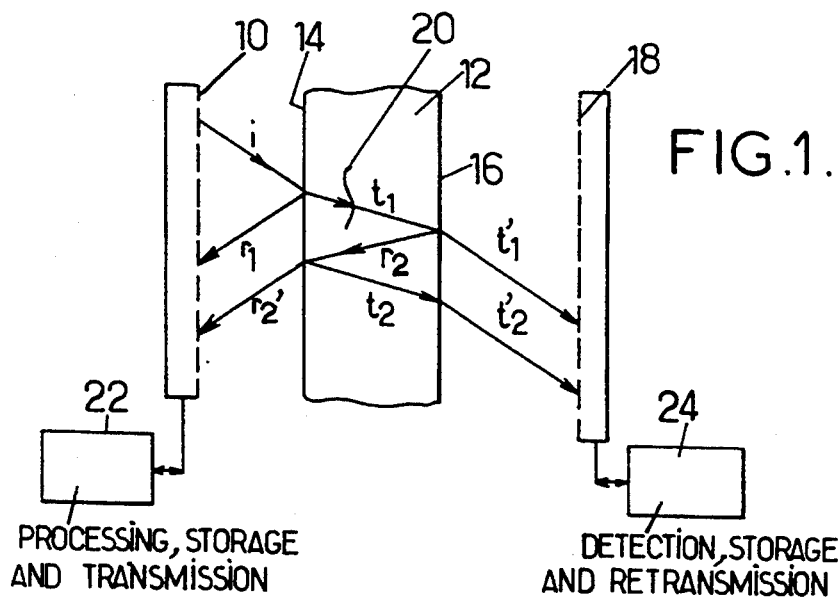
FIG.1.
FIG.9.
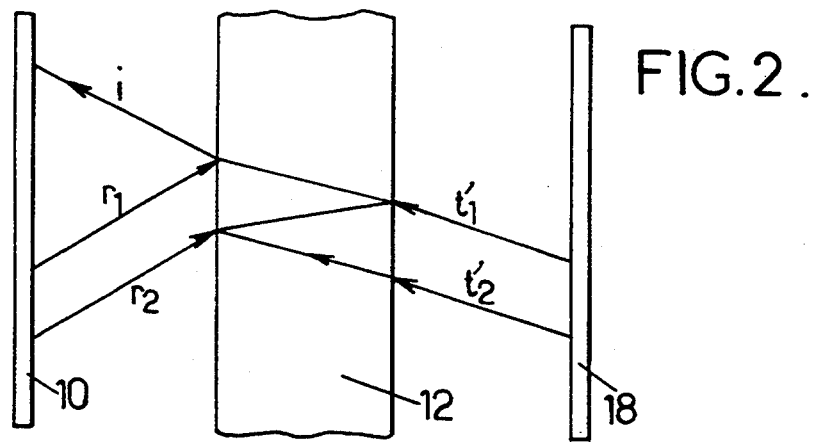
FIG.2.
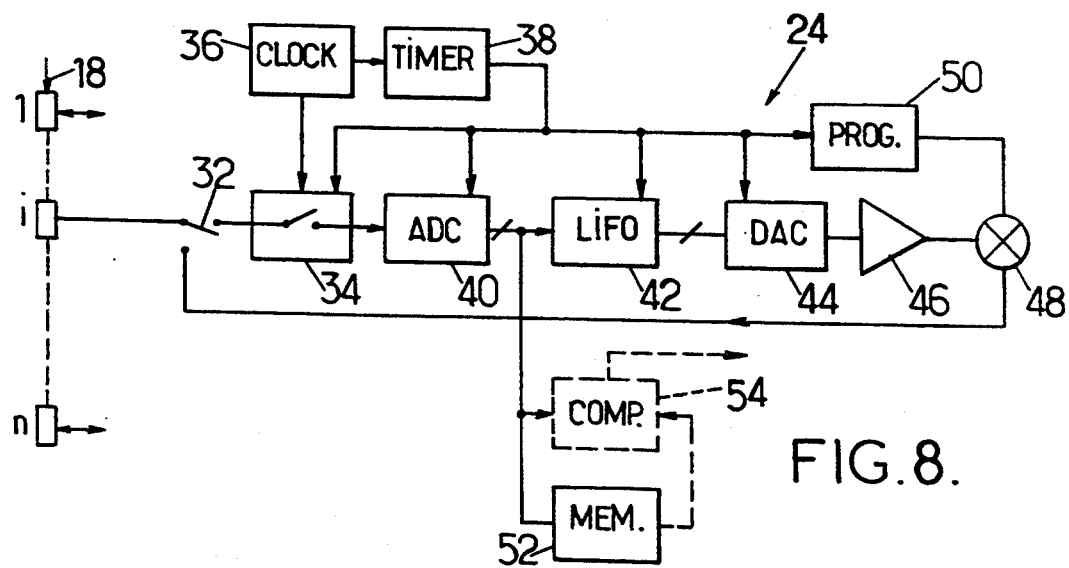
FIG.8.

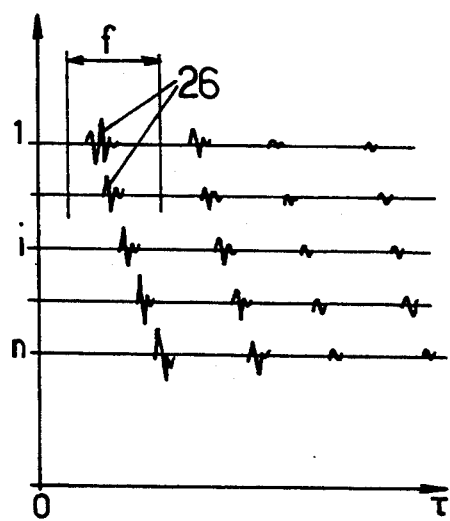
FIG.3.
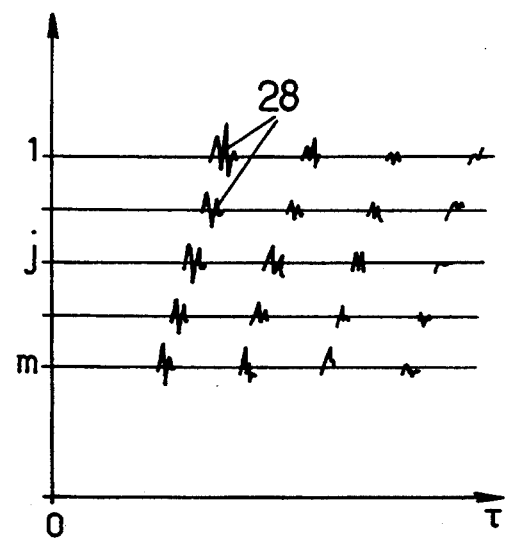
FIG.4.
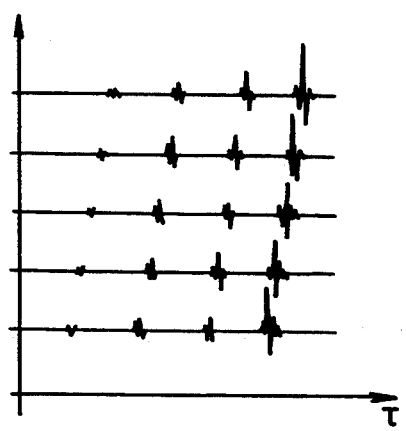
FIG.5.
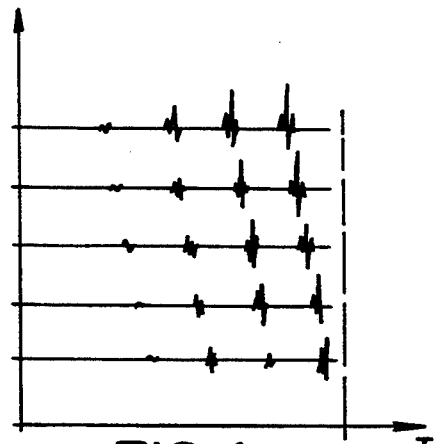
FIG.6.
FIG.7
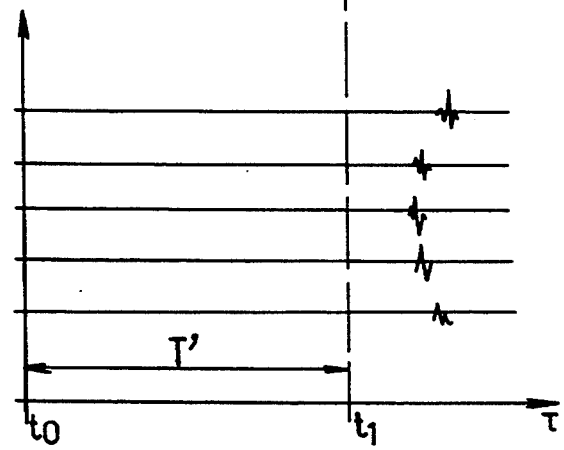

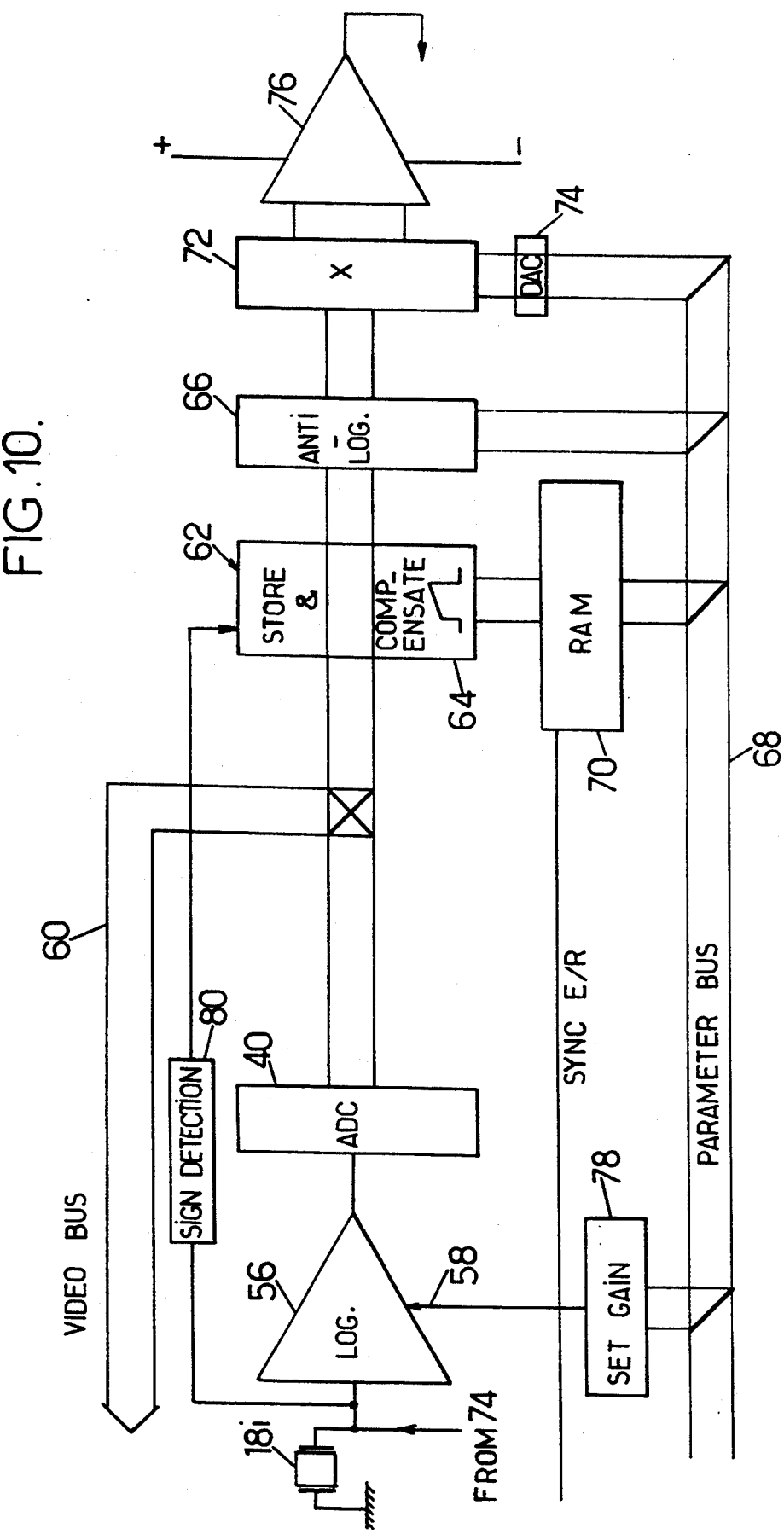

ULTRASONIC IMAGING METHOD AND APPARATUS, USING TIME INVERSION OR SIGNALS

BACKGROUND OF THE DISCLOSURE

The present invention relates to methods and apparatuses for non destructive internal inspection of pieces by ultrasound, by comparing the response from a piece to be inspected with a reference response constituted either by the response from a piece that is taken to be satisfactory, or from an average value of responses from a plurality of pieces that are unlikely to present the same defect, or else from a mathematical model.

A particular important, but not exclusive, application of the invention lies in detecting faults, breaks, cracks, and non-uniformities in various materials such as metals, composites, and ceramics.

Numerous apparatuses for ultrasound inspection of pieces are already known that operate in transmission or in reflection. When an in-depth image is to be made of a piece by using an array of transducers as a source and as a receiver, a major difficulty arises from the fact that the echo reflected from the input interface into the piece is much more intense than any echo which may be reflected from defects and the said interface echo masks the echoes to be identified. The problem is further aggravated when the piece is complex in shape and/or non-uniform in structure.

Since it is not possible to eliminate the interfering echo from the input interface (and possibly also echoes that come from multiple reflections on the input and output interfaces), the invention seeks to compensate for it.

To do this, the invention uses a technique that may be called "time-reversed or time inverted ultrasonic amplification" as described in document EP-A-0 383 650 to which reference may be made. That technique is itself based on the identity of waveform equations when time is reversed, even when dealing with signals over a very wide frequency band. According to document EP-A-0 383 650, a zone to be inspected is initially "illuminated" from one or more transducers belonging to a two-dimensional array, and the echoes from the material are recorded in electronic memories located behind each individual transducer. In a second stage, the received signals are re-emitted after inverting their time distributions, and possibly also their waveforms. In other words, the signals received last are returned first.

The effect of variation in absorption as a function of depth can be compensated by changing the gain with which the time-reversed or time inverted wave is amplified as a function of the to and fro time.

The purpose of such time reversal was to return a wave in the event of a wave representing an echo from a defect to the defect with an increased amplitude. The divergent wave front returned by a defect of arbitrary shape was thus optimally refocussed.

SUMMARY OF THE INVENTION

The present invention makes a different use of time reversal and uses two arrays of transducers straddling the piece to be inspected. The purpose of time reversal is determining an optimum shape of the signals to be applied to the two arrays of transducers in order to cancel by interference the echo reflected from at least one of the interfaces of the piece.

The invention will be better understood from a simplified description with reference to FIG. 1. For greater simplicity, a wave front is not described, but only an isolated incident ray i.

Such an incident ray from an array 10 of ultrasonic transducers gives rise, within a piece 12, to a first reflected ray $r_1$ reflected by the input interface 14 and to a first refracted ray $t_1$. A fraction of the energy in the reflected ray $t_1$ is reflected by the output interface 16 and gives rise to a reflected ray $r_2$ and to a refracted ray $t'_1$. The echo signal constituted by the sum of signals $r_1$, $r'_2$, ... can be sensed, using the transducers of array 10 or another array placed on the same side of the piece. Similarly, the refracted signal constituted by the sum of signals $t'_1$, $t'_2$, ... can be sensed and recorded using transducers in a second array 18. Recording may be analogue or digital, with timing of the echo signal and of the refracted signal relative to the signal as emitted.

When the stored signals are derived from an input wave having well-determined characteristics (e.g. by calibrating the signals emerging the transducers of matrix 10), two records or storages are thus obtained which constitute a space-time signature representative of the piece 12 in one-to-one relationship. This result is obtained regardless of the waveform applied to the piece 12 by the array of transducers 10. The wave may be a plane wave, a converging spherical wave optionally focussed inside the piece, a diverging spherical wave, a cylindrical wave, etc.; the waveform of the signal may be a damped wave train, a Dirac pulse, etc.

If the concept of time-reversed mirror is then implemented by returning, from the two arrays of transducers that served for obtaining the record or storage, time-reversed signals whose waveforms and distribution in time (or at least whose distribution) are reversed relative to the record, then the wave fronts generated at the two interfaces of the piece will recreate, in reversed time sequence, the wave "scene" as explained below with reference to FIG. 2.

It can be observed between the piece 12 and the array 10, a single wave front whose direction of propagation is reversed relative to the incident wave i.

In addition, no wave front will be reflected between the piece 12 and the array 18: the array 18 will therefore receive no echo.

The invention makes use of this observation to determine the differences that exist between different pieces.

According to an aspect of the invention there is provided a method for internally inspecting pieces by ultrasound, comprising the steps of:

(a) illuminating a first piece with an ultrasound beam from a first array of transducers excited by stored excitation signals;

(b) sensing reflected echo signals received by transducers, which may be the transducers of the first array, and storing the waveform and the time distribution of said echo signals;

(c) simultaneously sensing refracted signals received by transducers belonging to a second array placed opposite to the first relative to the piece and storing the waveform and time distribution of said refracted signals received by the transducers of the second array;

(d) replacing the first piece with a piece to be inspected having the same shape and occupying the same location, and applying energization signals to each of the transducers used in steps (b) and (c), the energization signals being obtained by time reversal of said stored waveforms and said time distribution; and (e) sensing the signals received by the transducers of the second network.

If the inspected piece is satisfactory, i.e. identical to the first piece which constitutes a reference, then no signal is received during step (e).

Any non-zero signal can only originate from defects situated in the piece. The defects can then be located by thresholding (detecting return signals greater than a threshold) or by a formating operation in a receive processing channel.

Steps (a), (b) and (c) may be carried out once only, on a standard piece that is assumed to be without defect. Alternatively, said steps may be repeated on a plurality of pieces that are not likely to have the same defects, in which case the distributions taken during steps (b) and (c) are averaged before being time reversed. By a finite element calculation, it is possible to determine space-time signatures of a piece, which is equivalent to modeling above steps (a) to (c) mathematically, and which makes it possible to eliminate possible defects in the reference piece, but at the costs of performing a calculation that becomes complicated when the piece is complex in shape. Finally, the piece to be inspected can be used itself by retaining only the large echoes that come from reflections on the interfaces.

Proper operation of the method can be verified by repeating step (d) after replacing the piece to be inspected with the first piece: the transducers in the second array should receive no signal.

Whichever technique is used, the presence of a defect within the piece, e.g. as shown at 20 in FIG. 1, will give rise to additional reflections upon time reversal that will cause signals to be applied to the transducers of the second array.

There is also provided an apparatus for implementing the above-defined method; the apparatus comprises a first array of transducers and a second array of transducers confronting the first array, the transducers in the two arrays being provided with respective processing channels each comprising a receiver circuit, a memory for storing the signal sensed by the respective transducer, and a power transmitter controlled by the memory programmable either to comply with a time distribution which is reverse of that stored in the memory or to comply with a distribution that is determined by calculating transmission times and waveforms.

Except when attenuation in the pieces to be inspected is low, it is necessary to compensate for the effect of attenuation. For an echo signal, attenuation varies responsive to the depth of the echo source; for signals that result from refracted ultrasound, attenuation varies in particular responsive to the number of successive paths through the piece. For compensation, each channel associated with a transducer may include either an amplifier followed by a controlled attenuator, or an amplifier whose gain is controlled by a programming circuit. Another solution consists in amplifying the signal logarithmically, in adding a linearly varying signal to the logarithmic signal, and then in exponentiating before transmission. This technique is simplest, given that ramp generators are readily available.

The invention will be better understood from the following description of a particular embodiment given by way of non-limiting example. The description refers to the accompanying drawing.

BRIEF DESCRIPTION OF THE DRAWINGS

FIG. 1, already mentioned, is a theoretical diagram showing steps taken for the purpose of reconstructing a wave front by time reversal;

FIG. 2 is similar to FIG. 1 and shows the reconstruction of a wave front by time reversal;

FIGS. 3 and 4 are timing diagrams showing one example of electrical signals from various transducers, respectively for detecing the reflected signal and for detecting the refracted signal;

FIGS. 5 and 6 are timing diagrams showing an example of signals emitted by the transducers previously used for detection purposes, for illuminating the piece to be inspected;

FIG. 7 is a timing diagram showing signals received by the transducers that previously received the refracted signal, when a defect is present in the piece to be inspected;

FIG. 8 is a block diagram of a channel associated with a transducer in an apparatus constituting a particular embodiment of the invention;

FIG. 9 shows one possible disposition for the transducers when inspecting a piece that has non-planar interfaces; and FIG. 10 is a block diagram showing a modification of the apparatus shown in FIG. 8.

DETAILED DESCRIPTION

An implementation of the method of the invention is described below for comparing a reference piece and successive pieces to be inspected that have exactly the same shape and that are placed in exactly the same position in the inspection apparatus. For example, the piece may be a metal body such as a billette of alloy or it may be a shaped piece such as a blade for a turbine or blower.

During a first step, the reference piece 12 is illuminated by a broad beam provided by an array 10 of transducers that are excited by an energization signal stored in a memory (not shown). This signal may be constituted by a short pulse applied with a same phase to all transducers 1, . . . i, . . . , n and originating from the same generator as that which is used later. The transducers in the array 10 may be distributed in a two-dimensional matrix or along a line, providing it is acceptable to obtain an image by scanning. The transducers may be conventional, comprising piezoelectric ceramic plates. It is often advantageous to use transducers that have a central resonant frequency of from a few hundreds of kHz to a few MHz.

The second step of the method consists in sensing both the echo signal and the refracted signal, and in storing the waveforms and the relative positions of the signals.

The transducers, which should deliver signals to be provided that are representative of the echo, may be the same as the transducers in array 10 or they may be transducers in another array placed on the same side of the piece 12 as the array 10. In the only case considered below, the same transducers in the same array 10 are used both for delivering the ultrasound beam and for receiving the echo but this is not essential. This array of transducers is then connected to a unit 22 for processing, storing, and retransmitting signals, and an embodiment thereof is described below. It should be observed at this point that each transducer in the array 10 is connected to a processing channel including a receiver circuit and a memory for storing the signal sensed by the transducer, and a programmable transmitter controlled either by said memory with a time distribution that is reversed relative to that for storage in the memory, or else by another memory in which predetermined waveforms and/or predetermined emission times have been stored.

However, such identity is not essential. In particular, for emission purposes, it is possible to use only some of the transducers that are used for receiving the echo.

The transducers that sense the transmitted ultrasound beam belong to a second array 18 placed opposite to the array 10 with respect to the piece 12, and associated with a unit 24 for detecting, storing, and retransmitting signals, which unit may be similar to the unit 22.

FIG. 3 shows an example of the aspect that the electrical signals may have at the outputs from the various transducers in the array 10 together with their positions in time when the electrical signal energizing the transducers is constituted by a short pulse.

FIG. 4 shows the appearance that the electrical signals may then have at the outputs of transducers 1, ... j, ..., m of array 18. In FIG. 3, the damped wave trains 26 correspond to the first reflection on the input interface 14. In FIG. 4, the damped wave trains 28 correspond to the shortest travel indicated in FIG. 1 by i, $t_1$, $t'_1$. Records are thus available at the end of the second step which may be considered as constituting a signature of piece 12.

It should be observed that the various wave fronts recorded by the transducers in the arrays 10 and 18 become attenuated over time because of multiple reflections. After a sufficient length of time T, recording by the arrays 10 (FIG. 3) and 18 (FIG. 4) may be stopped.

During a following step, the signals stored in the units 22 and 24 are used to energize the transducers of arrays 10 and 18 after time reversal of the distribution and of the waveforms of the signals. Insofar as the transducers present a linear response or present the same response characteristic on transmission and on reception, the waveform produced by energizing the arrays 10 and 18 is an exact reproduction of the original wave. Only its intensity is changed due to the attenuation that takes place in the piece 12 and possibly also during the path prior to entering the piece or after leaving it. This may be verified. However it is not essential. It suffices merely to store the response of the transducer in the array 10 and in the array 18.

In the embodiment described above, the third step consists in replacing the reference piece 12 with a piece to be inspected. To perform the invention, the piece to be inspected should be on the same position as the position occupied by the reference piece.

To verify that it is indeed in the same position, one technique consists in cross-correlating the signals stored in the unit 22 for the reference pieced in a time window f selected to include the first reflection on the interface 14 and the signals received from the piece to be inspected, and then in seeking to maximize said cross-correlation by moving the part. This boils down to clamping the sampling period during transmission.

In general, it normally suffices merely to check the geometry with an accuracy that is compatible with the wavelength of the ultrasounds used, about 1 millimeter.

Once the piece to be inspected has been put into place, the last step consists in again energizing the transducers in the arrays 10 and 18 with time reversal of the distribution and of the waveforms of the stored signals (FIGS. 5 and 6) and in detecting the signals provided by the array 18 operating as a receiver (FIG. 7). The signals can be due only to defects in the piece since interface echoes have been eliminated.

Defects can then be detected or an image of the inside of the piece to be inspected can then be displayed by processing the N signals provided by the N transducers of the array 18. These signals are taken only from a time $t_1$ that is delayed relative to the transmission time $t_0$ by a time interval T' which is long enough to ensure that the array 18 has finished transmitting the entire sequence of time-reversed signals.

After being sensed and stored, generally in digital form, the signals from a possible defect can be located by various processes.

A first process consists in using a method of forming reception channels, of the type already described in document EP-A-0 383 650, to which reference may be made. For each possible defect position, all of the signals are firstly delayed relative to one another by applying a delay law that corresponds to focussing on the assumed location of the defect, and the delayed signals are then summed. The amplitude of the summed signal for each focussing position is displayed and an image is built up by step-by-step reconstruction.

That process serves to provide an image that is satisfactory. However, reconstruction time is long. If the only purpose is to detect that at defect is present, e.g. to trigger an alarm, then a threshold detector suffices for triggering an alarm each time one of the signals (or a predetermined minimum number of the signals) exceeds the threshold.

When reconstruction is performed step-by-step, an overall view of the piece can be provided that is similar to an echography.

For detection purposes, the circuit 24 includes a plurality of channels each associated with a transducer. FIG. 8 shows a single channel, associated with transducer i. Since that the same array 18 is used for emission and for reception, the channel includes a switch 32 for switching between emission and reception and storage.

The components concerned with reception comprise a sampler 34 for providing analogue sample of the signal received by the transducer i at a frequency of a clock 36 (generally several MHz) during time intervals fixed by a timer 38. This time interval must be long enough to enable all of the echo signals $r_1$ and all of the refracted signals $t'_1$ to be received. It is useful to provide reception time windows that are longer, making it possible also to receive the signals $r'_2$ and $t'_2$, or more generally all signals of significant amplitude. The sampler 34 is followed by an analogue-to-digital converter (ADC) 40. When attenuation effects are compensated by means other than digital computation, a conversion over ten bits is generally enough to represent the dynamic range in reflection (for $r_1$) and in transmission (for $t'_1$). Bytes each representing a respective sample are stored in a memory 42 organized as a last-in, first-out (LIFO) stack, of sufficient capacity to store all of the samples received during the time fixed by the timer 38. Time reversal is performed over that time period only.

The timer 38 is designed so as to cause sampling to begin after a predetermined time from the first energizatation of the array 10, time estimation being easy given knowledge of the speed of ultrasound propagation and of the distance between the array 10 and the input interface 14.

The timer 38 is also designed to cause transmission of the reversed wavefront to begin at a predetermined time after the end of the echo. The transmission components of the channel associated with the transducer i comprise a digital-to-analogue converter (DAC) 44 followed by an amplifier 46. In the example as shown, the channel further includes an attenuator 48 whose function is to compensate for variations in attenuation responsive to depth. The attenuation coefficient of the attenuator 48 is changed in time by a programmer 50 in which a function is stored in digital form. The function is the reverse of the absorption negative exponential function in the medium passed through. The programmer is started by the timer 38.

The channel associated with a transducer i may further include a comparator 54 whose function is to compare the successive samples received in response to time-reversed emission and the samples obtained in response to time-reversed emission on the reference piece, as stored in a memory 52.

The unit 22 may have the same structure as the unit 24, except that its timer 38 must take account of the fact that the first signal appears at the output of array 10 starting at a time that is different from that at which the signal appears on array 18.

The arrays of transducers may be of any shape, providing they illuminate the whole piece or at least the whole of the portion thereof that is to be inspected. Nevertheless, it is preferable to adapt the shape of the arrays to the shape of the piece, and, for example, when the piece is cylindrical, to use arrays in the form of cylindrical sectors, as shown in FIG. 5.

FIG. 10 shows a possible embodiment of the acquisition and transmission portions of an inspection apparatus similar to that of FIG. 8.

Each transducer, 18$_i$ for example, is connected to a logarithmic amplifier 56 whose gain is controlled by the voltage applied to an input 58. The output of the amplifier 56 is applied to an analogue-to-digital converter 40 which samples the signal and quantifies each sample, e.g. on ten bits. The digitized signal may be applied to a video bus 60 for display purposes. The signal is also applied to a storage and depth compensation assembly 62 that includes a RAM memory and an adder/subtractor serving to add the signal to a digital saw tooth stored in a memory 64. The saw tooth may be defined by a parameter bus 68, via a processing RAM 70, the bus being a 4-bit bus for example.

The portion of the apparatus in FIG. 10 used for re-transmission comprises an exponentiation (antilogarithmic circuit 66, which may be a RAM loaded from the bus 68 and constituting a conversion table. The resulting digital signals (e.g. on 12-bits) are applied to a correction and conversion circuit 72 which receives multiplying coefficients from the parameter bus 68. These coefficients may be provided on 4-bits and they may be put into analogue form by a digital-to-analogue converter 74. Multiplication is then performed in analogue form in unit 72. Finally, the output signal is applied to a linear amplifier 76 that feeds transducer 18$_i$. The initial gain of the reception amplifier 56 may be set by the bus 68 via a gain register 78.

Since the digital signals obtained after lag conversion are devoid of sign, a separate bit, delivered by a sign detector 80 is added to each digital word in the storage RAM enabling full recovery at the output of the DAC.

I claim:

1. Method for internal inspection of a piece to be inspected, comprising the steps of:
   (a) illuminating a first piece with an ultrasound beam through a propagation medium, said first piece having a shape and location;
   (b) storing waveforms and time distributions of reflection responsive signals delivered by a plurality of transducers of a first array, said transducers of said first array being located to receive echoes of said ultrasound beam of an input interface between said first piece and said propagation medium;
   (c) simultaneously with step (b), storing waveforms and time distributions of refraction responsive signals delivered by a plurality of transducers of a second array placed opposite to the first array relative to the first piece to receive ultrasound energy of said ultrasound beam which has been refracted by said input interface and by an output interface of said first piece;
   (d) replacing said first piece with a piece to be inspected having the same shape and location as said first piece;
   (e) applying energization signals to said transducers of said first array and of said second array, the energization signals being obtained by time inversion of the waveforms and the time distributions stored during steps (b) and (c); and
   (f) sensing signals received by the transducers of said second array responsive to said energization signals.

2. Method according to claim 1, further comprising checking whether said piece to be inspected is at the same location as said first piece by cross correlating:
   said reflection responsive signals obtained during steps (b), and
   other reflection responsive signals obtained during steps (b), and
   other reflection responsive signals obtained by repeating steps (a) and (b) after said first piece has been replaced with said piece to be tested.

3. Method for internal inspection of a piece to be inspected,
   comprising preliminary steps comprising finite element computation on a virtual piece having a same shape and a same composition as a piece to be inspected and devoid of internal defects, by:
   (a) determining and storing waveforms and time distributions of reflected signals which would be delivered by a plurality of transducers belonging to a first array, constructed and located to receive echoes from an input interface of said virtual piece if illuminated by a predetermined ultrasound beam, and
   (b) determining and storing waveforms and time distributions of refracted signals which would be delivered by a plurality of transducers of a second array, constructed and located to receive ultrasound signals refracted through said input interface and by an output interface of said virtual piece if illuminated by said predetermined ultrasound beam;
   and further comprising the steps of:
   (c) placing said piece to be inspected between an actual first array of transducers and an actual second array of transducers having the same constructions and locations as the first array and second array used for computation during preliminary steps (a) and (b), (d) applying energization signals to each of the transducers of said actual first array and actual second array, the energization signals being derived from the waveforms and the time distributions stored during steps (a) and (b) by the time inversion; and (e) collecting signals received by the transducers of said actual second array.

4. Device for internal ultrasound inspection of a piece to be inspected comprising:

a first array of transducers, each transducer of said first array being provided with a processing channel having a receiver circuit, a first memory for storing a signal sensed by said each transducer, and a power transmitter controlled by said first memory, said first memory comprising a controllable memory means for successively storing a first waveform of the signal sensed respectively by said each transducer of the first array responsive to ultrasound echoes and for delivering a control signal to said each transducer of said first array which is obtained by time inversion of said first waveform;

a second array of transducers located at a distance from the first array, each transducer of said second array being provided with a processing channel having a receiver circuit, a second memory for storing a signal sensed by said each transducer of said second array and a power transmitter controlled by said second memory, said second memory comprising controllable memory means for successively storing a second waveform of the signal sensed by said each transducer of said second array responsive to refracted ultrasounds, and for delivering a control signal to said each transducer of said second array which is obtained by the time inversion of said second waveform; and sequencing means for controlling the memories of the processing channels of said first array and of said second array in such a way that the control signals delivered to said transducers of said first and second arrays have a time distribution which is inverted as compared to a time distribution of the ultrasound echoes and refracted ultrasounds, respectively and for detecting signals received from said transducers of said second array responsive to application of said control signals.

5. Method according to claim 1, wherein, during steps (b) and (c), said reflection responsive signals and said refraction responsive signals are stored only for time periods selected for storing only those signals of said reflection responsive signals and refraction responsive signals which are generated by reflection and refraction on and across said input and output interfaces.

6. Method according to claim 1, wherein, steps (b) and (c) are repeated on a plurality of first pieces unlikely to have identical internal defects so as to obtain a plurality of waveforms and a plurality of time distributions and wherein said plurality of waveforms and said plurality of time distributions are averaged before step (d).

7. Method according to claim 1, wherein said first piece is illuminated during step (a) by energizing at least some of the transducers of said first array.

8. Device according to claim 4, wherein each said processing channel includes a respective transducer associated therewith and comprises, in series relation, a reception path having a logarithmic amplifier connected to receive signals from the respective transducer associated with the processing channel, an analog-to-digital converter, addressable memory means for depth absorption compensation, and an exponentiation circuit and further comprises a sign detector for sensing polarity of each of the signals received from the respective transducer and delivering a polarity-representing bit to said first memory or said second memory depending whether the respective transducer associated with the processing channel belongs to the first array or the second array.

* * * * *